United States Patent
Sakaguchi et al.

(10) Patent No.: US 9,439,818 B2
(45) Date of Patent: Sep. 13, 2016

(54) DISPOSABLE DIAPER

(75) Inventors: Satoru Sakaguchi, Kagawa (JP);
Yasuhiro Yamanaka, Kagawa (JP)

(73) Assignee: UNICHARM CORPORATION,
Ehime (JP)

( * ) Notice: Subject to any disclaimer, the term of this patent is extended or adjusted under 35 U.S.C. 154(b) by 126 days.

(21) Appl. No.: 14/241,342

(22) PCT Filed: Aug. 24, 2012

(86) PCT No.: PCT/JP2012/005310
§ 371 (c)(1),
(2), (4) Date: Jun. 5, 2014

(87) PCT Pub. No.: WO2013/031157
PCT Pub. Date: Mar. 7, 2013

(65) Prior Publication Data
US 2014/0316364 A1    Oct. 23, 2014

(30) Foreign Application Priority Data

Aug. 26, 2011 (JP) .................................. 2011-185341

(51) Int. Cl.
*A61F 13/56* (2006.01)
*A61F 13/62* (2006.01)

(52) U.S. Cl.
CPC ....... *A61F 13/5655* (2013.01); *A61F 13/5633* (2013.01); *A61F 13/622* (2013.01); *A61F 13/625* (2013.01)

(58) Field of Classification Search
CPC ........... A61F 13/5622; A61F 13/5655; A61F 13/62; A61F 13/625

USPC ......................................................... 604/391
See application file for complete search history.

(56) References Cited

U.S. PATENT DOCUMENTS

| | | | |
|---|---|---|---|
| 2003/0009144 A1* | 1/2003 | Tanzer | A61F 13/5622 604/391 |
| 2003/0045854 A1* | 3/2003 | Yoshioka | A61F 13/5622 604/386 |
| 2008/0087569 A1* | 4/2008 | Ponomarenko | A61F 13/495 206/570 |

FOREIGN PATENT DOCUMENTS

| | | |
|---|---|---|
| CN | 101410080 A | 4/2009 |
| EP | 2810631 A1 | 12/2014 |
| EP | 2835124 A1 | 2/2015 |
| JP | 60-119944 A | 6/1985 |
| JP | 2001-046436 A | 2/2001 |

(Continued)

OTHER PUBLICATIONS

Extended European Search Report dated Mar. 27, 2015, corresponding to European patent application No. 12828999.8.

(Continued)

*Primary Examiner* — Peter S Vasat
(74) *Attorney, Agent, or Firm* — Hauptman Ham, LLP

(57) ABSTRACT

A fastening tape 100 of a disposable diaper 10 has a base sheet 120 configured by a nonwoven fabric, and a hook sheet 110 in which a plurality of engagement hooks are provided. The KES flexural rigidity value of the entire fastening tape existent region $S_{ALL}$ in which the fastening tape 100 is provided, in a longitudinal direction $D_L$ of the absorbent main body, is 11.755 gf.cm² or less.

10 Claims, 5 Drawing Sheets

(56) References Cited

FOREIGN PATENT DOCUMENTS

| JP | 2003-070840 A | 3/2003 |
|---|---|---|
| JP | 2005-40231 A | 2/2005 |
| JP | 2007-512080 A | 5/2007 |
| JP | 2007-516036 A | 6/2007 |
| JP | 2008-188349 A | 8/2008 |
| JP | 2009-000352 A | 1/2009 |
| JP | 2011-72736 A | 4/2011 |
| TW | 201110948 A1 | 4/2011 |
| WO | 2006/071211 A1 | 7/2006 |

OTHER PUBLICATIONS

Office Action dated Jun. 16, 2015, corresponding to Chinese patent application No. 201280041720.1.

International Search Report mailed Nov. 27, 2011 in International Application No. PCT/JP2012/005310, mailed Aug. 24, 2012.

Written Opinion of the International Searching Authority mailed Nov. 27, 2011 in International Application No. PCT/JP2012/005310, mailed Aug. 24, 2012.

Office Action mailed Oct. 28, 2014, corresponding to Chinese patent application No. 201280041720.1.

Office Action mailed Sep. 8, 2015, corresponding to Japanese Patent Application No. 2011-185341.

Office Action mailed Sep. 24, 2015, corresponding to Taiwanese Patent Application No. 101130849.

Office Action in JP Application No. 2011-185341, mailed Apr. 12, 2016.

* cited by examiner

DISPOSABLE DIAPER

RELATED APPLICATIONS

The present application is a National Phase of International Application No. PCT/JP2012/005310, filed Aug. 24, 2012, and claims priority from Japanese Application No. JP 2011-185341 filed Aug. 26, 2011.

TECHNICAL FIELD

The present disclosure relates to a disposable diaper including a fastening tape in either one of a front waistline portion or a back waistline portion.

BACKGROUND ART

A so-called open-type disposable diaper including fastening tapes for fastening on to the side flaps of the back waistline portion (or the front waistline portion) is provided widely as a disposable diaper used primarily for infants and toddlers. The open-type disposable diaper including the fastening tapes, such as that described above, is widely used for newborns as well as infants and toddlers in particular due to the ease of wearing and removing.

In such an open-type disposable diaper, a structure in which a proximal end of the skin contact surface side of the fastening tape is covered with side flaps (nonwoven fabric), which are softer than the fastening tape, is known (for example, Patent Literature 1). According to such a disposable diaper, because the stimulation of the skin of the infant or toddler by the fastening tape is prevented, it is difficult for the infant or toddler to experience an unpleasant feeling and pain.

CITATION LIST

Patent Literature

[PTL 1] Japanese Patent Unexamined Publication No. 2003-70840 (FIG. 1)

SUMMARY OF INVENTION

Technical Problem

It is known that by providing various stimuli after birth to the brain of a newborn, an infant or a toddler (hereinafter, infant or toddler), the transfer network of information spreads around, and the growth of the transfer network is remarkable in infancy, that is, from the time of birth up to a year.

Specifically, more than the necessary number of nerve cells (neurons) exist in an infant, and during infancy, more than a few trillion times of the actually used number of synapses are formed. Therefore, the neurons determined as unnecessary are removed, and the synapses that do not receive a stimulus degenerate. That is, various operations are performed in an infant, and the brain and body of an infant grow according to the stimuli obtained from these operations.

Because the growth of a neuron is hindered by stress and promoted by an appropriate stimulus, it is vital that an infant does not get any unpleasant feeling and pain. Particularly, in the stage where an infant starts remembering the movement of the body, even when the infant has only the power to move the body (for example, the legs), the infant stops that movement if he/she gets an unpleasant feeling. On the other hand, in the absence of an unpleasant feeling, it becomes easy for an infant to start repeating that movement.

Furthermore, the spinal column of an infant presents a C-curve in which the thoracic spine and the lumbar spine curve sharply towards the back. Such a posture makes it easy for an infant to make use of the muscles naturally, and also stabilizes the breathing, which enables maintaining perfect alertness. A stimulus in the prefect alert state promotes cerebral development. Bending the legs towards the body when sleeping in a supine state, and holding bent legs with both hands are postures peculiar to infancy.

In the conventional open-type disposable diaper, when the legs are bent from the posture in which the aforementioned C-curve is presented, the fastening tape easily comes in contact with the body because the fastening tape exists in the area of the inguinal opening. Furthermore, because the fastening tape is hard, a high pressure is exerted on the part of the body near the fastening tape, and the infant might be prevented from bending the legs. Particularly, because the portion near the inguinal opening is a range where a leg can move greatly, and the portion where the skin is thin and the lymph nodes exist, the infant is sensitive to unpleasant feelings and pain.

Therefore, the present invention has been achieved in view of such a situation, and an object thereof is to provide a disposable diaper, by which it becomes more difficult for the wearer, particularly, an infant or toddler, to get an unpleasant feeling and pain when the legs are bent, and an adverse effect on the growth of the infant or toddler can be prevented effectively.

Solution to Problem

The feature of the present invention is summarized in that a disposable diaper is provided, which is configured by a front waistline portion, a back waistline portion, and a crotch portion, and comprises: a longitudinally elongated absorbent main body including an absorber having liquid retention property; and side flaps provided in at least a part of the side edges in a widthwise direction of the absorbent main body; and a fastening tape installed on the side flaps, and configured to extend out towards the outer side of the widthwise direction of the absorbent main body from one side of the front waistline portion or the back waistline portion, so as to be fastened at the other side of the front waistline portion or the back waistline portion, wherein the fastening tape has a base sheet configured by a nonwoven fabric, and a hook sheet in which a plurality of engagement hooks are provided, and the KES flexural rigidity value of an entire fastening tape existent region in which the fastening tape is provided, in a longitudinal direction of the absorbent main body, is 11.755 gf.cm$^2$ or less.

Advantageous Effects of Invention

According to a characteristic of the present invention, it is possible to provide a disposable diaper, by which it becomes more difficult for the wearer, particularly, an infant or toddler, to get an unpleasant feeling and pain when the legs are bent, and an adverse effect on the growth of the infant or toddler can be effectively prevented.

DESCRIPTION OF EMBODIMENTS

Figure 1:
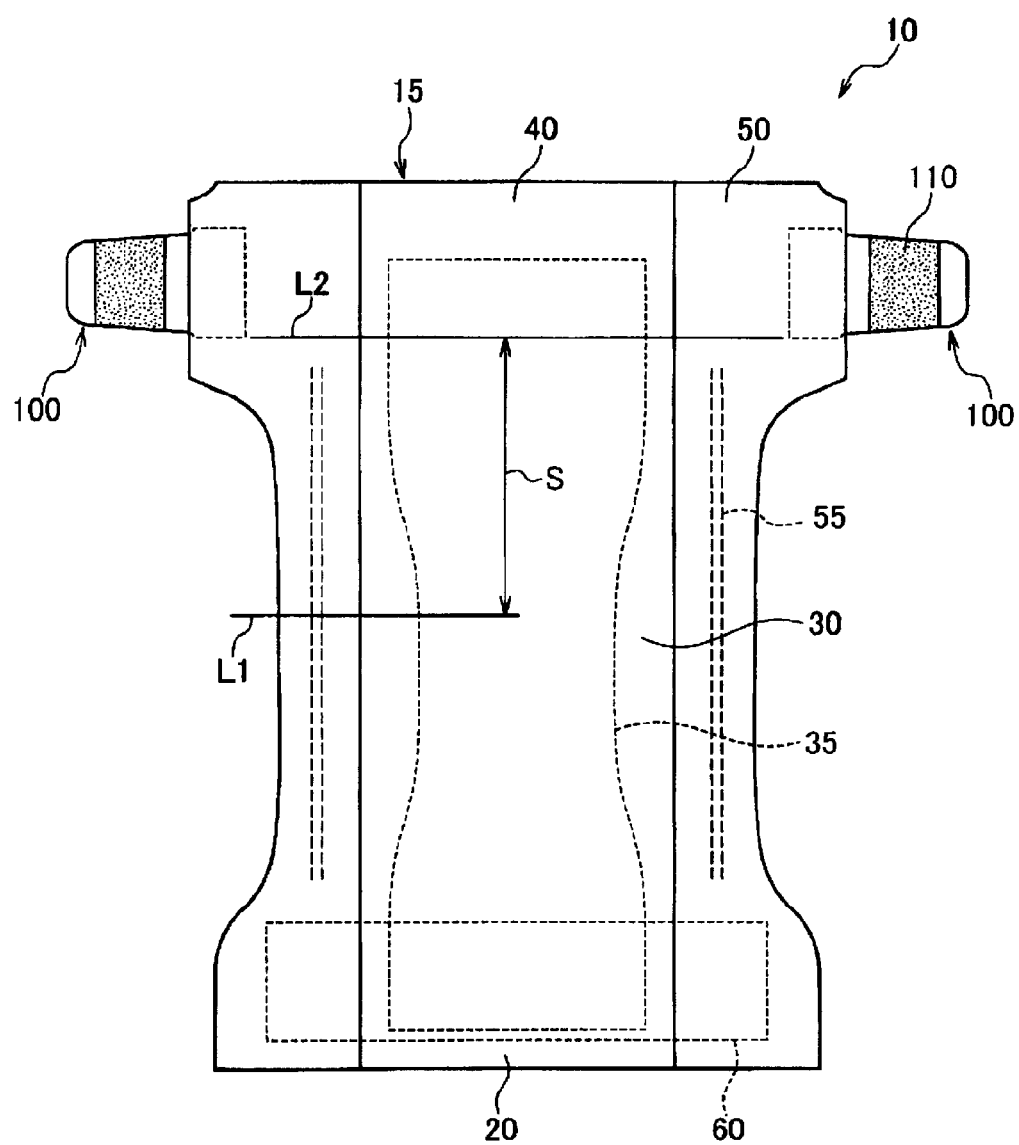
FIG. 1 is a plan view of a disposable diaper 10 according to an embodiment of the present invention.

Next, an embodiment of a disposable diaper according to the present invention is explained with reference to drawings. In the following description of the drawings, the same or similar reference numerals are used to designate the same or similar parts. The drawings are schematic representations and are not drawn to scale unless otherwise specified. Moreover, the drawings do not necessarily reflect the actual dimensional relationships and ratios of components. Therefore, specific dimensions or the like should be determined in consideration of the following description. In addition, relations or ratios among such dimensions may be different from one drawing to another.

Accordingly, specific dimensions should be determined in consideration of the explanation below. Moreover, among the drawings, the respective dimensional relations or ratios may differ.

(1) Configuration of the Disposable Diaper

FIG. 1 is a plan view of a disposable diaper 10 according to the present embodiment. As shown in FIG. 1, the disposable diaper 10 is an open-type diaper having a front waistline portion 20, a crotch portion 20, and a back waistline portion 40. The disposable diaper 10 can be used favorably for infants and toddlers in particular.

An absorbent main body 15 is configured by the front waistline portion 20, the crotch portion 30, and the back waistline portion 40. The absorbent main body 15 has a longitudinally elongated shape including an absorber 35 with liquid retention property. In the present embodiment, the absorber 35 may be provided across the front waistline portion 20, the crotch portion 30, and the back waistline portion 40, as shown. The absorber 35 may have a shape such that the width of the absorber in the central portion of the longitudinal direction $D_L$ of the absorbent main body 15 is narrow, as shown. The shape of the absorber 35 is not limited to the shape shown in FIG. 1, and may also be a simple rectangle. Furthermore, the absorber 35 must at least be provided in the crotch portion 30 but may not extend to the front and back waistline portions.

The absorbent main body 15 is similar to the conventional open-type disposable diaper, and can be configured appropriately by using well-known members and material. Furthermore, the absorbent main body 15 may also include a liquid-permeable topsheet, side gathers provided in the side edges of the absorbent main body 15 along the longitudinal direction $D_L$, and waist gathers provided in the back waistline portion 40 along the widthwise direction $D_W$, which are not shown in the figure.

Side flaps 50 are provided in the side edges of the absorbent main body 15 in the widthwise direction $D_W$. The side flaps 50 may be configured by one layer of nonwoven fabric or a plurality of layers of nonwoven fabric layered on each other.

In the present embodiment, the side flaps 50 may be provided across the entire region of the absorbent main body 15 in the longitudinal direction $D_L$, as shown. That is, the side flaps 50 may be provided such that they extend from the front waistline portion 20 up to the back waistline portion 40. The width of the side flaps 50 corresponding to the crotch portion 30 may be than the width of the side flaps 50 corresponding to the front waistline portion 20 and the back waistline portion 40. The side flaps 50 need not necessarily be provided across the entire region of the absorbent main body 15 in the longitudinal direction $D_L$, for example, the side flaps may be provided only in the region corresponding to the back waistline portion 40.

Furthermore, in the side edges of the absorbent main body 15 in the widthwise direction $D_W$, specifically, in the side flaps 50, stretchable leg elastic members 55 may be provided along the longitudinal direction $D_L$ of the absorbent main body 15. The absorbent main body 15 is contracted in the longitudinal direction $D_L$ by the leg elastic members 55. The absorbent main body 15 thus contracted can be, particularly, stretched in the longitudinal direction $D_L$ at the back waistline portion 40 side.

Specifically, the percentage of stretch of the absorbent main body 15 in the longitudinal direction $D_L$, in the region S between the straight line L1 passing through the center of the absorbent main body 15 in the longitudinal direction $D_L$ and the straight line L2 parallel to the widthwise direction $D_W$ of the absorbent main body 15 passing through the outer edges of the fastening tape 100 positioned towards the crotch portion 30, may be set to 130% or more. Furthermore, the percentage of stretch is desired to be 250% or less. If the percentage of stretch is 250% or less, it may be ensured that the disposable diaper 10 does not over-stretch and dislocation of the disposable diaper at the time of wearing may be effectively avoided. The percentage of stretch is calculated for the portion in which the leg elastic members 55 are arranged, by measuring the distance between the straight lines L1 and L2 in the state in which the disposable diaper 10 is stretched up to the point where no wrinkles are formed and also in the natural state, respectively, and then dividing the distance in the stretched state by the distance in the natural state.

A fastening tape 100 is preferably installed on each of the side flaps 50. Specifically, each fastening tape 100 extends towards the outer side of the absorbent main body 15 in the widthwise direction $D_W$ from the back waistline portion 40. Each fastening tape 100 is configured such that it may be fastened to the front waistline portion 20 when the diaper is worn. A hook sheet 110 (not shown in FIG. 1; see FIG. 2) of the fastening tape 100 is preferably configured to engage with the target tape 60 and is preferably provided on the back sheet 70 (not shown in FIG. 1; see FIG. 3) side of the front waistline portion 20.

The fastening tapes 100 may be installed on the side flaps 50 to extend towards the outer side of the absorbent main body 15 in the widthwise direction $D_W$ from the front waistline portion 20, rather than the back waistline portion 40, and in the case of infants and toddlers for whom the disposable diaper is changed mostly while sleeping in the supine state, the fastening tape 100 is desired to be installed in the back waistline portion 40.

(2) Configuration of the Fastening Tape

Figure 2:
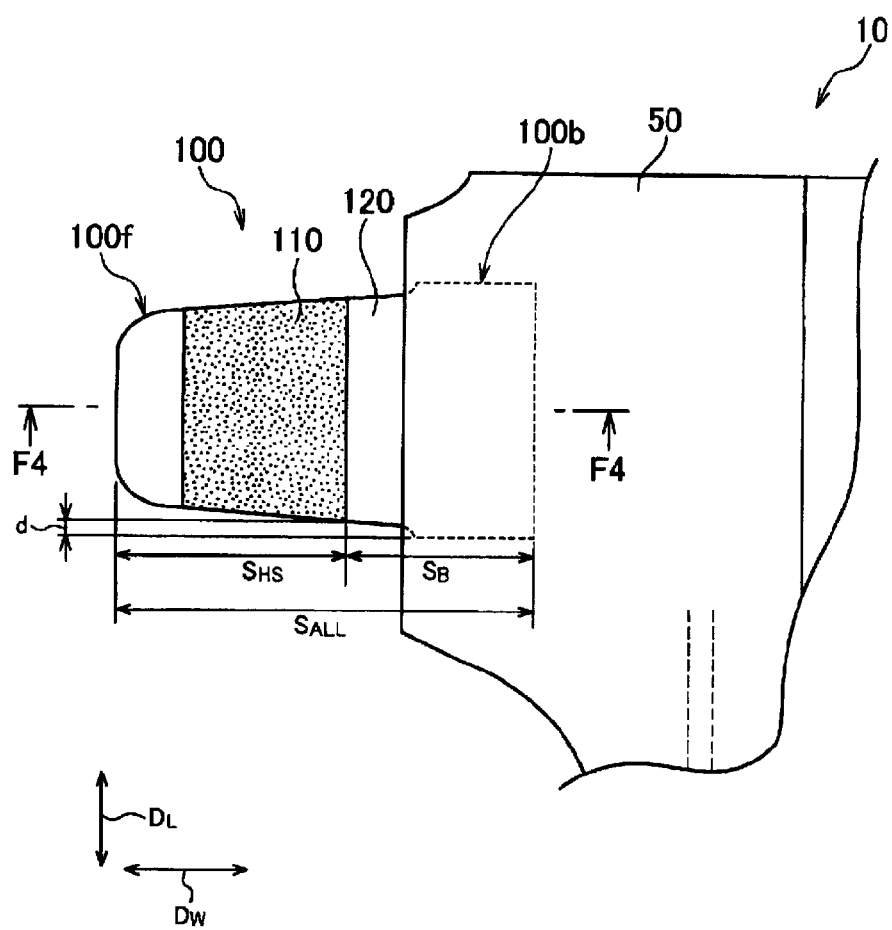
FIG. 2 is an enlarged view of the fastening tape 100 portion (side flap 50 side) of the disposable diaper 10 according to the embodiment of the present invention.
Figure 3:
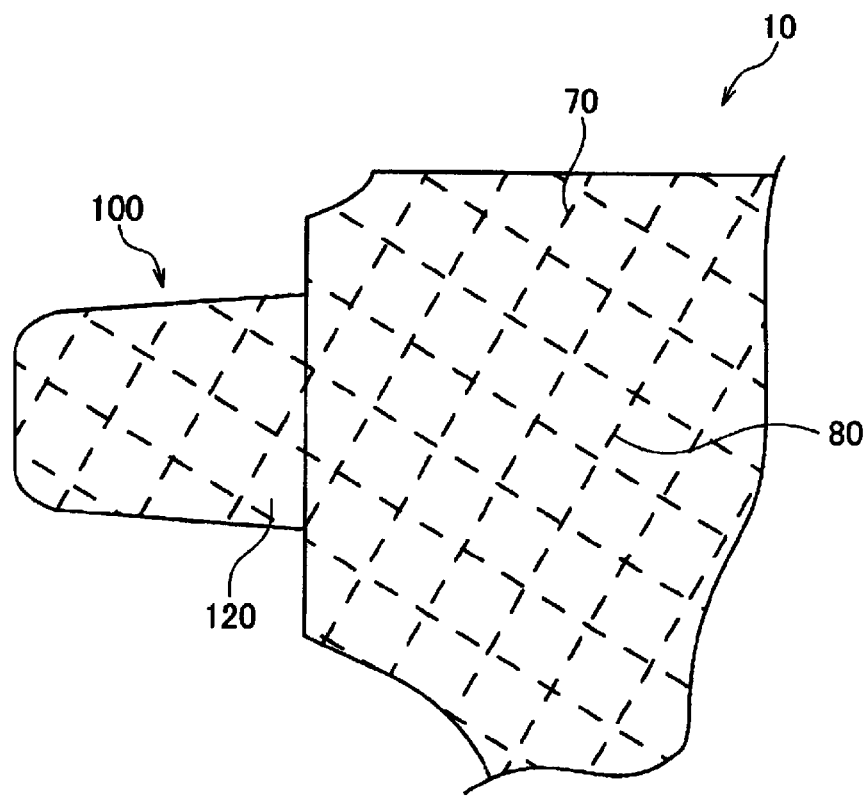
FIG. 3 is an enlarged view of the fastening tape 100 portion (backsheet 70 side) of the disposable diaper 10 according to the embodiment of the present invention.
Figure 4:
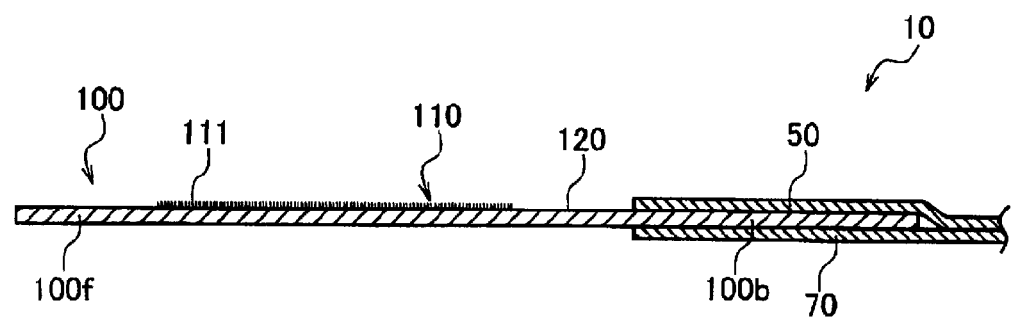
FIG. 4 is a cross-sectional view of the disposable diaper 10 along an F4-F4 line shown in FIG. 2.

Next, the preferred shape of the fastening tape 100 is explained with reference to FIGS. 2 through FIG. 4. FIG. 2 is an enlarged view of the fastening tape 100 portion (side flap 50 side) of the disposable diaper 10. FIG. 3 is an enlarged view of the fastening tape 100 portion (backsheet 70 side) of the disposable diaper 10. FIG. 4 is a cross-sectional view of the disposable diaper 10 along an F4-F4 line shown in FIG. 2.

As shown in FIG. 2 through FIG. 4, the fastening tape 100 is installed in the region of the side flap 50 corresponding to the back waistline portion 40 (see FIG. 1). The fastening tape 100 has a hook sheet 110 in which a plurality of engagement hooks 111 are provided, and a base sheet 120 formed by a nonwoven fabric.

The hook sheet 110 is joined with the base sheet 120. The hook sheet 110 and the base sheet 120 are desired to be joined such that the rigidity of the fastening tape 100 does not become more than necessary. Specifically, the hook sheet 110 and the base sheet 120 are desired to be joined by a hot-melt adhesive applied intermittently in dot shape, line shape, or spiral shape. The hook sheet 110 and the base sheet 120 may also be joined with a heat seal or any other suitable joining means, as will be readily appreciated to those skilled in the art.

Furthermore, in order to reduce the rigidity of the hook sheet 110, various well-known methods, such as reducing the thickness of the base portion of the hook sheet 110, and increasing the gap formed in the base portion, can be used. For example, a hook sheet having a base portion with a thickness of 25 to 150 um, as described in Japanese Unexamined Patent Application Publication (Translation of PCT Application) No. 2007-516036, can be used.

In the present embodiment, the size of the hook sheet 110 may be larger than the size of the conventional standard hook sheet. Specifically, the size in the widthwise direction $D_w$ and the longitudinal direction $D_L$, may be set as 20 to 30 mm and 30 to 50 mm, respectively. The size of the conventional standard hook sheet in the widthwise direction $D_w$ and the longitudinal direction $D_L$ is 10 to 25 mm and 15 to 30 mm, respectively.

The base sheet 120 may be configured by one layer of nonwoven fabric or a plurality of layers of nonwoven fabric layered on each other. A nonwoven fabric manufactured by a manufacturing method such as spun bond (SB) or spun bond-melt blown-spun bond (SMS) can be used as the base sheet 120. The basis weight of the nonwoven fabric (or total basis weight in the case of a plurality of layers) configuring the base sheet 120 may be between 30 and 120 g/m², and is desired to be between 40 and 90 g/m². When the basis weight is more than 30 g/m², the strength for maintaining the disposable diaper 10 is easily retained, and at the time of using the fastening tape 100, the frequency of breakage in the region in which the hook sheet 110 does not exist does not increase. On the other hand, when the basis weight is 120 g/m² or less, it can be ensured that the flexural rigidity of the fastening tape 100 does not become too high. More specifically, in case that the base sheet 120 is configured by one layer, it is preferable that nonwoven fabric having the basis weight of 30 through 120 g/m² is used and thickness of the base portion of the hook sheet 110 is between 25 um and 105 um. It is more preferable that nonwoven fabric having the basis weight of 40 through 80 g/m² is used and thickness of the base portion of the hook sheet 110 is between 25 um and 45 um. In case that the base sheet 120 is configured by a plurality of layers (two or three layers), it is preferable that single or plural nonwoven fabric having the basis weight less than 30 g/m² and single or plural nonwoven fabric having the basis weight of 30 through 120 g/m² are used, and thickness of the base portion of the hook sheet 110 is between 25 um and 105 um. It is more preferable that single or plural nonwoven fabric having the basis weight less than 30 g/m² and single or plural nonwoven fabric having the basis weight of 30 through 90 g/m² are used, and thickness of the base portion of the hook sheet 110 is between 25 um and 45 um.

Furthermore, in the present embodiment, the fastening tape 100 may have a shape such that as the fastening tape 100 extends from the proximal end 100b installed on the side flap 50 towards the free end 100f positioned on the opposite side of the proximal end 100b and transversely outside the side flap, the width in the longitudinal direction $D_L$ of the absorbent main body 15 reduces. The difference d between the width of the fastening tape 100 along the longitudinal direction $D_L$ of the absorbent main body 15 in the proximal end 100b and the width of the fastening tape 100 along the longitudinal direction $D_L$ of the absorbent main body 15 at the end of the hook sheet existent region $S_{HS}$, towards the proximal end 100b, may be 7.5 mm or less, and is desired to be 5.0 mm or less.

As shown in FIG. 3, embossed portions 80 may be formed in the backsheet 70 of the disposable diaper 10. Furthermore, the embossed portions 80 having a similar form may be formed in the fastening tape 100, specifically, in the base sheet 120 as well. That is, the outer surface of the base sheet 120, which is the surface at the opposite side of the surface in which the hook sheet 110 is provided, and the outer surface of the absorbent main body 15 are desired to have substantially the same form or the same color tone.

As shown in FIG. 4, the proximal end 100b of the fastening tape 100 may be installed between the side flap 50 and the backsheet 70. The fastening tape 100, the side flap 50 and the backsheet 70 are also desired to be joined by a hot-melt adhesive applied intermittently in dot shape, line shape, or spiral shape, as described above.

(3) Flexural Rigidity and Flexural Recovery of the Fastening Tape

Next, the KES flexural rigidity value and the KES flexural recovery value of the fastening tape 100 are explained. The specific method of measuring the KES flexural rigidity value and the KES flexural recovery value is described later.

(3.1) Flexural Rigidity

In the present embodiment, the KES flexural rigidity value of the entire fastening tape existent region $S_{ALL}$ (see FIG. 2), where the fastening tape 100 is provided, in the longitudinal direction $D_L$, is 11.755 gf.cm2 or less. It is preferable that the KES flexural rigidity value is 2.569 gf.cm2 or more, and more preferably the KES flexural rigidity value is 3.576 gf.cm2 or more. Note that the entire fastening tape existent region consists of the entire fastening tape and the portion of the side flap/backsheet that overlaps with the fastening tape. Furthermore, in the fastening tape existent region $S_{ALL}$, the KES flexural rigidity value in the longitudinal direction $D_L$ of the hook sheet existent region $S_{HS}$, where the hook sheet 110 is provided, is preferably 10.298 gf.cm² or less. It is preferable that the KES flexural rigidity value is 1.837 gf.cm² or more, and more preferably the KES flexural rigidity value is 2.416 gf.cm² or more. The hook sheet existent region $S_{HS}$ also includes the portion of the fixing tape towards the free end 100f side from the portion in which the hook sheet 110 is provided. In other words, the hook sheet existent region includes the portion of the fixing tape from the transverse inner edge of the hook sheet outwards in the widthwise direction.

Additionally, when the KES flexural rigidity value (gf.cm2/cm) per unit length of the hook sheet existent region $S_{HS}$ in the longitudinal direction $D_L$ is assumed as $B_1$. and the KES flexural rigidity value (gf.cm2/cm) per unit length of the hook sheet non-existent region $S_B$ in which the hook sheet 110 is not provided, in the fastening tape existent region $S_{ALL}$, in the longitudinal direction $D_L$, is assumed as $B_2$, the KES flexural rigidity ratio $B_2/B_1$ preferably satisfies the relation of 0.8 to 1.20. It is more preferable that the KES flexural rigidity value satisfies the relationship of $B_1<B_2$.

Furthermore, the KES flexural rigidity value per unit length of the hook sheet existent region $S_{HS}$ in the widthwise direction $D_w$ is preferably 2.848 gf.cm2/cm or less. [0038J (3.2) Flexural recovery In the present embodiment, the KES flexural recovery value of the entire fastening tape existent region $S_{ALL}$, in the longitudinal direction $D_L$, is preferably 13.401 gf.cm or less. It is preferable that the KES flexural recovery value is 4.380 gf.cm2 or more, and more preferably the KES flexural recovery value is 6.657 gf.cm2 or more.

Furthermore, the KES flexural recovery value in the longitudinal direction DL of the hook sheet existent region SHs is preferably 8.430 gf.cm or less. It is preferable that the KES flexural recovery value is 2.207 gf.cm² or more, and more preferably the KES flexural recovery value is 3.924 gf.cm² or more.

(4) Examples

Next, non-limiting examples of the present invention are explained. Table 1 shows an overview of the configuration and test results of the fastening tape according to example 1 through example 6, and the fastening tape according to comparative example 1 through comparative example 4 (hereinafter, appropriately abbreviated simply as examples and comparative examples). The "+" sign in Table 1 indicates a laminate of several layers. For example, the base sheet in Example 1 is a laminate of two spun-bond nonwoven fabrics, one having a basis weight of 80 g/m² the other having a basis weight of 27 g/m².

Furthermore, the overall dimension (fastening tape existent region $S_{ALL}$) in the widthwise direction $D_w$ of the fastening tape according to the examples and the comparative examples was 67 mm, the dimension of the hook sheet existent region $S_{HS}$ (including the free end 100f) was 38 mm, and the dimension of the hook sheet non-existent region $S_B$ was 29 mm.

Furthermore, the ease of movement of the legs of the wearer (infant) was also tested by using the samples.

Hereinafter, the details of the measurement methods and the test results of each test are explained in detail.

(4.1) Method of Experiments;

(4.1.1) Flexural Properties

The flexural properties of the fastening tape were measured by using the KES flexural property measuring machine manufactured by KATO TECH CO., LTD. Specifically, the B value (flexural rigidity) and the 2HB value (flexural recovery) were measured.

Specifically, the details of the KES method are explained in "The Standardization and Analysis of Hand Evaluation" 2nd Edition (The Hand Evaluation and Standardization Committee, the Textile Machinery Society of Japan, Issued on Jul. 10, 1980). Therefore, as regards the method of measuring each mechanical property, only the measurement conditions related to the measurement are explained.

The flexural properties were measured by using KES-FB2 manufactured by KATO TECH CO., LTD., by fixing each sample (the entire fastening tape) between the chucks, bending to the front up to maximum curvature +2.5 cm−1, and then bending to the back up to maximum curvature −2.5 cm−1, and then returning to the origin.

Figure 5:
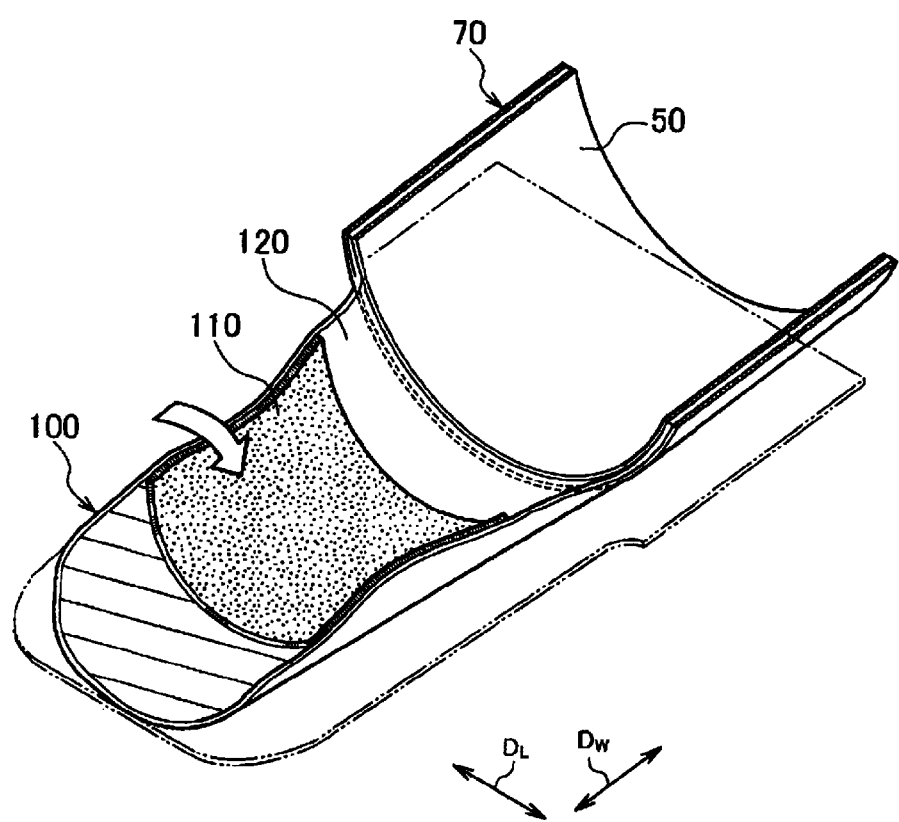
FIG. 5 is an explanatory diagram of a direction of bending when the flexural properties of the fastening tape 100 are measured.

FIG. 5 is an explanatory diagram of a direction of bending when the flexural properties of the fastening tape 100 are measured. As shown in FIG. 5, the fastening tape 100 is bent up to the above-mentioned curvature in the longitudinal direction $D_L$ or the widthwise direction $D_w$, by using KES-FB2 (not shown in the figure) manufactured by KATO TECH CO., LTD. In FIG. 5, the solid line shows the shape of the fastening tape 100 when the fastening tape 100 is bent along the longitudinal direction $D_L$ of the absorbent main body 15, and the two-dot chain line shows the shape of the fastening tape 100 before being bent. Furthermore, as shown in FIG. 5, the fastening tape 100 used for the test included the side flap 50 and the backsheet 70 overlapping the

TABLE 1

| | base sheet | | hook sheet | | side flaps | | back sheet | |
| --- | --- | --- | --- | --- | --- | --- | --- | --- |
| | type of nonwoven fabric | basis weight (gsm) | basis weight | thickness (μm) | type of nonwoven fabric | basis weight | type of nonwoven fabric | basis weight |
| Example 1 | spun bond | 80 + 27 | 40 | 45 | spun bond | | spun bond | |
| Example 2 | ↑ | 80 | 40 | 45 | ↑ | 15 | ↑ | 27 |
| Example 3 | ↑ | 60 + 27 | 40 | 45 | ↑ | 15 | ↑ | 27 |
| Example 4 | ↑ | 40 + 20 + 27 | 40 | 45 | ↑ | 15 | ↑ | 27 |
| Example 5 | ↑ | 30 + 27 | 40 | 45 | ↑ | 15 | ↑ | 27 |
| Example 6 | ↑ | 40 + 27 | 100 | 105 | ↑ | 15 | ↑ | 27 |
| Comparative Example 1 | ↑ | 80 | 100 | 105 | ↑ | 17 | ↑ | 17 |
| Comparative Example 2 | ↑ | 80 | 108 | 105 | ↑ | 17 | ↑ | 17 |
| Comparative Example 3 | ↑ | 70 | 108 | 105 | ↑ | 17 | ↑ | 17 |
| Comparative Example 4 | ↑ | 15 + 27 | 40 | 45 | ↑ | 17 | ↑ | 17 |

As shown in table 1, a test was performed regarding the flexural properties (flexural rigidity and flexural recovery) of the fastening tape by using a plurality of samples having different types of nonwoven fabric used in the fastening tape, and different basis weights or thickness of the hook sheet (thickness of the base portion of the hook sheet 110 excluding the height of the engagement hooks 111).

fastening tape 100. That is the test piece is obtained by cutting out the fastening tape from the side flap/backsheet by cutting along its periphery. The portion of the side flap/backsheet that overlaps with the fastening tape forms part of the entire fastening tape existent region and therefore forms part of the test piece.

After the sample was made perpendicular (to the horizontal) in order to reduce the effect of gravity, the flexural rigidity B [gf.cm²/cm] was calculated from the inclination when the inclination of the bending moment with respect to the curvature becomes almost constant after bending towards the front is started. Furthermore, the flexural recovery 2HB [gf.cm/cm] was calculated from the hysteresis width. By integrating the entire width of the individually measured samples with the KES flexural rigidity value B and the flexural recovery value 2HB per unit length, which have thus been calculated, the flexural rigidity value [gf.cm²] and the flexural recovery value [gf.cm] of the entire sample to be measured were calculated.

(4.1.2) Ease of Movement of Legs

A trial production of the disposable diaper 10 (size S) shown in FIG. 1 was performed regarding the ease of movement of the legs of the wearer, and only the fastening tape was changed and tested in each example and comparative example.

Specifically, 20 disposable diapers, in which the fastening tape of the example 1 through example 6, and comparative example 1 through comparative example 4 was installed, were provided to each of 30 monitored persons (persons taking care of infants aged three to six months), and the persons were asked to fill in a questionnaire after using the provided disposable diapers. Furthermore, in order to support the results of the questionnaire answered by these monitored persons, dolls were made to wear the same disposable diapers, and the extent up to which the legs could be raised until the exertion of a pressure (20 hPa) at which an infant can feel a load, was measured.

More specifically, in order to compare the fastening tapes, "Moony (registered trademark) Size S Nenne-Jitate" manufactured by the commercial company Unicharm Corporation was used to prepare samples by replacing the fastening tape portion, the side flaps portion used to fix the fastening tape, and the backsheet portion, from a position of approx. 20 mm on the inner side of the fixed portion, and the test was performed.

Next, each sample was put on onto a doll, and the pressure (pressure of wearing) at the position of the inguinal portion of the legs was measured. The position of wearing the disposable diaper on the doll was kept substantially the same for each sample, with the appropriate wearing position being the standard. As a standard, the disposable diaper was put on at a position close to where a line along the inguinal portion, which is a base line between the femoral portion and the waistline portion of the doll, and the lower half region of the fastening tape overlap.

As for the position of installing the tape in the waistline direction, the position of installing the fastening tape (position at the outer end of the hook sheet) was a position that is 50 mm from the center of the widthwise direction of the product, and a substantially disc-shaped air pack with a diameter of 15 mm was inserted between the disposable diaper and the doll such that approx. the upper half overlapped the fastening tape, at the position where the fastening tape comes in contact with the inguinal opening.

In such a state, the tightening of the disposable diaper is to the extent where one index finger can be inserted in the area around the waist. Specifically, minor adjustments are made such that the tightening of the disposable diaper is to the extent that one index finger can be inserted around the waist, and a pressure of 1 to 3 hPa can be exerted on the air pack. In the initial state, the doll was placed in the supine state with the legs at almost a horizontal level.

In this state, the legs of the doll were raised vertically upwards, and at the point of time when the pressure (wearing pressure) became 20 hPa, a photograph was taken from the level horizontal direction, and the crossing angle of the virtual center line of the trunk and the virtual center line around the leg was measured. The measurement was performed 10 times, and the average value of the crossing angle was assumed as the leg-raise angle.

As for the doll, an S size silicon doll with the standard body type (waistline size at the navel portion: 39.5 cm, size of the inguinal portion around the legs: 25.0 cm, and waistline size passing through the apex of the hip portion: 37.5 cm) was used. Furthermore, for measuring the wearing pressure, a wearing pressure measuring device (contact pressure measuring system (AMI3037-SB-hP) manufactured by AMI Techno Co., Ltd.) was used.

Furthermore, the basis for assuming the wearing pressure as 20 hPa is from the understanding that the state at which a disposable diaper is pushed against the body to an extent that redness is generated on the skin of the wearer by the wearing pressure occurs at a pressure of 15 to 20 hPa, and therefore, the surface pressure was set to become 20 hPa or less.

(4.2) Results of the Tests (4.2.1) Flexural Properties

Table 2 shows the test results of the flexural properties of the entire fastening tape existent region $S_{ALL}$ in the longitudinal direction $D_L$.

TABLE 2

|  | B value flexural rigidity gf · cm2 | 2 HB value flexural recovery gf · cm |
|---|---|---|
| Example 1 | 11.3743 | 19.6851 |
| Example 2 | 7.5572 | 10.8633 |
| Example 3 | 6.1469 | 13.4009 |
| Example 4 | 4.0630 | 11.3743 |
| Example 5 | 3.5753 | 6.6567 |
| Example 6 | 11.7541 | 13.3761 |
| Comparative Example 1 | 20.5166 | 28.7437 |
| Comparative Example 2 | 18.0835 | 18.9084 |
| Comparative Example 3 | 16.9059 | 20.1457 |
| Comparative Example 4 | 2.5687 | 4.3796 |

As shown in Table 2, the value of the flexural rigidity B (hereinafter, the B value) of the fastening tape existent region $S_{ALL}$ according to the example 1 through example 6 was 11.755 gf.cm²/cm or less. Furthermore, the value of the flexural recovery 2HB (hereinafter, the 2HB value) of the fastening tape existent region $S_{ALL}$ according to the example 3 through example 5 was 13.401 gf.cm or less.

That is, in the example 1 through example 6, the flexural rigidity B is very low as compared to the comparative example 1 through comparative example 3, and particularly, in the example 3 through example 5, the value of the flexural recovery 2HB was also confirmed to be low.

On the other hand, because of too much flexibility in comparative example 4, tension could not be applied very well to the entire tape surface, which made it difficult to install on the disposable diaper main body. Additionally, even when removing the fastening tape, because of too much flexibility, even when the free end 100*f* is pulled to release the hook sheet 110 and the target tape 60, it is difficult to transfer the pressure on to the hook sheet 110, and a problem of difficulty in removing the fastening tape occurred. Furthermore, in comparative example 4, it was difficult to maintain the strength at which the fastening tape could be used without being torn at the time of installation.

Table 3 shows the test results of the flexural properties of the hook sheet existent region $S_{HS}$ in the longitudinal direction $D_L$.

TABLE 3

|  | B value flexural rigidity gf · cm2 | 2 HB value flexural recovery gf · cm |
|---|---|---|
| Example 1 | 6.8117 | 11.9994 |
| Example 2 | 3.7667 | 6.4316 |
| Example 3 | 3.2860 | 8.4292 |
| Example 4 | 2.4157 | 6.8815 |
| Example 5 | 2.5988 | 3.9239 |
| Example 6 | 10.2970 | 10.3278 |
| Comparative Example 1 | 12.5658 | 16.0110 |
| Comparative Example 2 | 13.7375 | 13.5198 |
| Comparative Example 3 | 12.9842 | 12.0894 |
| Comparative Example 4 | 1.8365 | 2.2061 |

As shown in Table 3, the B value of the hook sheet existent region $S_{HS}$ according to example 1 through example 6 was 10.298 gf.cm$^2$ or less. Furthermore, the 2HB value of the hook sheet existent region $S_{HS}$ according to example 3 through example 5 was 8.4292 gf.cm or less.

That is, in the example 1 through example 6, the flexural rigidity B is very low as compared to the comparative example 1 through comparative example 3, and particularly, in the example 3 through example 5, the value of the flexural recovery 2HB was also confirmed to be low.

Table 4 shows the test results of the KES flexural properties (gf.cm$^2$/cm, gf.cm/cm) per unit length of the hook sheet existent region $S_{HS}$. in the widthwise direction $D_w$.

TABLE 4

|  | B value flexural rigidity gf · cm2 | 2 HB value flexural recovery gf · cm |
|---|---|---|
| Example 1 | 2.8479 | 2.8283 |
| Example 2 | 0.8571 | 1.1429 |
| Example 3 | 1.2792 | 1.9893 |
| Example 4 | 0.9611 | 1.5846 |
| Example s | 0.3592 | 0.3230 |
| Example 6 | 1.9939 | 1.3977 |
| Comparative Example 1 | 4.6444 | 4.5778 |
| Comparative Example 2 | 4.4331 | 3.6107 |
| Comparative Example 3 | 3.2458 | 2.5038 |
| Comparative Example 4 | 0.2269 | 0.2040 |

As shown in Table 4, the B value of the hook sheet existent region SHs according to example 1 through example 6 was 2.8479 gf.cm$^2$/cm or less. Furthermore, the 2HB value of the hook sheet existent region $S_{HS}$ was 2.8283 gf.cm/cm or less. It is preferable that the B value is 0.227 gf.cm$^2$ or more, and more preferably the B value is 0.360 gf.cm$^2$ or more. It is preferable that the 2HB value is 0.205 gf.cm$^2$ or more, and more preferably the KES flexural recovery value is 0.324 gf.cm$^2$ or more.

That is, in example 1 through example 6, the values of the flexural rigidity B and the flexural recovery 2HB were confirmed to be very low as compared to the comparative example 1 through comparative example 3.

(4.2.2) Ease of Movement of Legs

As shown in Table 5, in the examples 1 to the example 6, when a five-stage evaluation ("Very easily movable", "Almost easily movable", "Cannot say anything", "Somewhat difficult to move", and "Almost difficult to move" was performed for the question "Do you think the baby can easily move its legs?" during the circulation of a questionnaire to the monitored persons, the results indicated that more than 80% persons felt either "Very easily movable" or "Almost easily movable".

Additionally, in the example 3 through example 5, more than five persons reported that positive movement of the legs was seen in the infants, as regards the ease of movement of the legs of the wearer (infant) in the free description column of the questionnaire. For example, details such as "The baby played well by holding the legs with both hands as compared to other normally used disposable diapers" were reported (indicated as "Good" in "Ease of movement of legs" in Table 5).

Furthermore, as shown in Table 5, in the test using dolls, a leg-raise angle of 60 degrees or more was secured in example 1 through example 6. On the other hand, in comparative example 1 through comparative example 3, in general, a leg-raise angle of only around 55 degrees could be secured. That is, it was confirmed that the leg-raise angle can be significantly increased in example 1 through example 6, as compared to comparative example 1 through comparative example 3, making it difficult to hinder the leg raising operation of the wearer.

TABLE 5

|  | Ease of movement of legs | Leg-raise angle | Pressure at the time of 90 degrees angle |
|---|---|---|---|
| Example 1 | Acceptable | 60 |  |
| Example 2 | Acceptable | 64 |  |
| Example 3 | Good | 90 | 8 hpa |
| Example 4 | Good | 90 | 5 hpa |
| Example 5 | Good | 90 | 4 hpa |
| Example 6 | Acceptable | 67 |  |
| Comparative Example 1 | Not good | 48 |  |
| Comparative Example 2 | Not good | 53 |  |
| Comparative Example 3 | Not good | 55 |  |
| Not worn | Good | — | 2 hpa |

(5) Operation and Effect

Next, an operation and effect of the aforementioned disposable diaper 10 is explained. The legs of a human are joined towards the front of the trunk. As a result, when the legs are moved forwards and backwards, the fastening tape of the disposable diaper is sandwiched between the inguinal portion in front of the portion around the leg and the abdominal portion, and the lower end of the fastening tape is in contact with the inguinal portion in front of the legs.

In the disposable diaper 10, because the KES flexural rigidity value of the entire fastening tape existent region $S_{ALL}$, in the longitudinal direction $D_L$, is 11.755 gf.cm2 or less, the fastening tape bends flexibly due to the force exerted when the lower end of the fastening tape comes in contact with the leg inguinal portion, and the wearer (infant and toddler) does not experience a feeling of discomfort at the time of moving the legs. As a result, because the legs can be moved further back and forth, the movement of the legs of the wearer becomes more of an activity, and particularly, it is difficult for the infant and toddler to get an unpleasant feeling and pain, and the adverse effect on the growth of the infant and toddler can be prevented effectively.

The KES flexural rigidity value is more preferably 6.147 gf.cm$^2$ or less.

Furthermore, in the above-mentioned embodiment, if the KES flexural rigidity value of the hook sheet existent region $S_{HS}$ in the longitudinal direction $D_L$ is 10.298 gf.cm$^2$ or less, the wearer does not experience a feeling of discomfort even in the portion of the hook sheet where load is exerted particularly due to the movement around the leg. Furthermore, if the KES flexural rigidity value per unit length of the hook sheet existent region $S_{HS}$ in the widthwise direction is 2.847 gf.cm$^2$/cm or less, it becomes easy for the fastening tape 100 to run along the abdominal portion and the ruggedness around the waist of the wearer, and it prevents the fastening tape 100 from partially coming off the target tape 60. Therefore, even when load is exerted on the fastening tape 100, the release of the fastening tape 100 from the target tape 60 due to folding of the fastening tape as a result of not following the ruggedness of the abdominal portion, can be prevented.

In the aforementioned embodiment, the percentage of stretch of the region S of the absorbent main body 15 in the longitudinal direction $D_L$ is preferably 130% or more. When the wearer moves the legs, the surface of the skin of the wearer extends and contracts, however, the surface of the side flaps 50 around the leg holes of the disposable diaper covers the surface of the skin at the hip portion side around the legs of the wearer. It was understood that the surface of the skin at this portion extended by around 25 to 30%, at the most.

By enabling the disposable diaper corresponding to the surface of the skin to extend by 30% or more, the side flaps 50 at the hip portion side around the legs follow the surface of the skin, and the sheets configuring the disposable diaper 10 can be stretched without sticking out, and therefore, the movement around the legs of the wearer is not hindered.

In the aforementioned embodiment (example 3 through example 5), the KES flexural recovery (2HB) value of the entire fastening tape existent region $S_{ALL}$, in the longitudinal direction $D_L$, may be 13.401 gf.cm or less. The 2HB value shows the degree of rebound of the fastening tape. In example 3 through example 5, after the wearer bends the legs and retains the state, the rebound of the fastening tape 100 is less, and it becomes easy for the wearer to maintain the state in which the legs are bent. Furthermore, it is difficult to exert a stimulus to the skin of the wearer. When the 2HB value is 13.401 gf.cm or less, even when the legs are bent by a large amount, the pressure received from the fastening tape is suppressed to a low value, and it is difficult to get a feeling of discomfort around the legs even in the state when the infant raises the legs and maintains the state.

In the aforementioned embodiment, specifically, in examples 1, 3, and 4, when the KES flexural rigidity value per unit length of the hook sheet existent region $S_{HS}$ in the longitudinal direction $D_L$ is assumed as $B_1$, and the KES flexural rigidity value per unit length of the hook sheet non-existent region $S_B$ in which the hook sheet 110 is not provided (including the region in which the hook sheet 110 is not provided, and which overlaps the side flaps 50), in the fastening tape existent region $S_{ALL}$, in the longitudinal direction $D_L$ is assumed as $B_2$, the KES flexural rigidity ratio B2/B1 preferably satisfies the relation of 0.80 to 1.20. Therefore, the curved state of the hook sheet non-existent region $S_B$ and the engagement portion of the target tape 60 is the same (the state in which wrinkling and curving is similar), and it becomes difficult for the fastening tape 100 to come off the target tape 60 as the pressure is not concentrated at any particular portion. Furthermore, the folding and rising of the fastening tape 100 becomes difficult to occur while maintaining the flexibility of the fastening tape 100, and it becomes difficult for the fastening tape 100 to come off the target tape 60.

Furthermore, when $B_2/B_1 > 1.0$, that is, $B_1 < B_2$, the flexibility of the hook sheet existent region $S_{HS}$ stands out, and therefore, the user can more certainly experience the flexibility of the hook sheet 110.

Additionally, in the present embodiment, because the rigidity of the hook sheet 110 and the base sheet 120 has been reduced, even when the hook sheet 110 is made larger than the size of the conventional standard hook sheet, the hook sheet 110 can be made to follow the shape of the disposable diaper 10 (specifically, the target tape 60), and can be engaged securely. In the case of the conventional standard hook sheet, although the size of the hook sheet was made as small as possible, and the hook sheet was engaged with the target tape at a small region for this reason, due to a high rigidity of the hook sheet, the change in the shape of the disposable diaper 10 could not be followed, and a feeling of discomfort was felt by the wearer, however, in the present embodiment, such a problem can also be evaded.

In the aforementioned embodiment, the shape of the fastening tape 100 installed in the side flaps 50 is preferably such that as the fastening tape 100 runs from the proximal end 100*b* thereof towards the free end 100*f* thereof, the width in the longitudinal direction $D_L$ narrows down. Therefore, it becomes easy to follow the shape of the inguinal portion around the legs of the wearer and the body type of the infants and toddlers in which their abdominal portion is often risen up.

In the aforementioned embodiment, the outer surface of the base sheet 120, which is the surface at the opposite side of the surface in which the hook sheet 110 is provided, and the outer surface of the absorbent main body 15 are desired to have substantially the same form (embossed portions 80). Therefore, it can be recognized by the user of the disposable diaper 10 that the fastening tape 100 forms one part with the disposable diaper 10, and is not a separate region. Because the sheet in the outermost layer of the disposable diaper (backsheet 70) is the portion that is frequently touched by the user (for example, the mother of the infant and toddler) when putting on the disposable diaper on the infant and toddler, a sheet that is soft to touch is preferably used.

In the case of the disposable diaper 10, because the fastening tape 100 is also flexible, the user can easily get a feeling that the fastening tape 100 is not a special object (foreign object), but same as the absorbent main body 15. As a result, the user can get an impression of a disposable diaper in which the wearer can easily move the legs.

(6) Other Embodiments

As described above, the present invention is disclosed through the above embodiments. However, it should not be interpreted that the statements and drawings constituting a part of the present disclosure limit the present invention. From this disclosure, a variety of alternate embodiments, examples, and applicable techniques will become apparent to one skilled in the art.

For example, in the aforementioned embodiment, embossed portions 80 are formed in the outer surface of the base sheet 120, which is the surface at the opposite side of the surface in which the hook sheet 110 is provided, and the outer surface of the absorbent main body 15, because of which the outer surface of the base sheet 120 and the outer surface of the absorbent main body 15 have substantially the same form, however, such a process need not necessarily be performed.

Furthermore, it is also possible to increase the B value in the free end 100*f* of the fastening tape 100 as compared to that in the base sheet 120. In such a case, this place becomes the place (tab) that is caught at the time of sealing and peeling the fastening tape 100, and the operability of the fastening tape 100 can be improved. Even in such a case, because the rigidity of the hook sheet existent region $S_{HS}$ can be made less than the aforementioned range, load is not exerted on the movement around the leg.

It was explained in the aforementioned embodiment that the disposable diaper 10 can be used favorably for infants and toddlers, however, the applicability of the present invention is not limited to a disposable diaper for infants and toddlers, for example, the present invention can definitely be applied even to a disposable diaper for children and adults.

As described above, needless to say, the present invention includes various embodiments and the like not described here. Therefore, the technical range of the present invention is to be defined only by the inventive specific matter according to the adequate claims from the above description.

REFERENCE SIGNS LIST

10 . . . Disposable diaper
15 . . . Absorbent main body
20 . . . Front waistline portion
30 . . . Crotch portion
35 . . . Absorber
40 . . . Back waistline portion
50 . . . Side flaps
55 . . . Leg elastic members
60 . . . Target tape
70 . . . Backsheet
80 . . . Embossed portion
100 . . . Fastening tape
100b . . . Proximal end
100f . . . Free end
110 . . . Hook sheet
111 . . . Engagement hook
120 . . . Base sheet
$S_{ALL}$ . . . Fastening tape existent region
$S_B$ . . . Hook sheet non-existent region
$S_{HS}$ . . . Hook sheet existent region

The invention claimed is:

1. A disposable diaper configured by a front waistline portion, a back waistline portion, and a crotch portion, said disposable diaper comprising:
   a longitudinally elongated absorbent main body including an absorber having liquid retention property;
   side flaps provided in at least a part of side edges of the absorbent main body in a widthwise direction of the absorbent main body; and
   a fastening tape installed on one of the side flaps, and configured
      to extend outwards in the widthwise direction from one of the front waistline portion or the back waistline portion, and
      to be fastened at the other of the front waistline portion or the back waistline portion,
   wherein
      the fastening tape has a base sheet configured by a nonwoven fabric, and a hook sheet having a plurality of engagement hooks,
   a KES flexural rigidity value, measured by the KES fabric bending test, of an entire fastening tape existent region in which the fastening tape is provided, in a longitudinal direction of the absorbent main body, is between 2.569 gf.cm$^2$ and 11.755 gf.cm$^2$,
   a KES flexural recovery value, measured by the KES fabric bending test, of the entire fastening tape existent region in the longitudinal direction of the absorbent main body is between 4.380 gf.cm and 13.401 gf.cm, and wherein the entire fastening tape existent region consists of the entire fastening tape, a portion of the side flap overlapping the entire fastening tape, and a portion of a backsheet overlapping the entire fastening tape.

2. The disposable diaper according to claim 1, wherein in the fastening tape existent region, the KES flexural rigidity value of a hook sheet existent region in which the hook sheet is provided, in the longitudinal direction of the absorbent main body, is 10.298 gf.cm$^2$ or less.

3. The disposable diaper according to claim 1, further comprising:
   leg elastic members stretchable and contractible in the longitudinal direction of the absorbent main body and provided along the side edges of the absorbent main body, wherein
   a percentage of stretch of the absorbent main body in the longitudinal direction in a region between a straight line passing through a center of the absorbent main body in the longitudinal direction and a straight line parallel to the widthwise direction of the absorbent main body and passing through an outer edge of the fastening tape positioned towards the crotch portion, is 130% or more.

4. The disposable diaper according to claim 1, wherein
   the KES flexural rigidity value per unit length of a hook sheet existent region, in which the hook sheet is provided, in the longitudinal direction of the absorbent main body is $B_1$,
   the KES flexural rigidity value per unit length of a hook sheet non-existent region, in which the hook sheet is not provided, in the fastening tape existent region, in the longitudinal direction of the absorbent main body is $B_2$, and
   the KES flexural rigidity ratio $B_2/B_1$ is from 0.80 to 1.20.

5. The disposable diaper according to claim 2, wherein the KES flexural rigidity value per unit length of the hook sheet existent region in the widthwise direction is 2.847 gf.cm$^2$/cm or less.

6. The disposable diaper according to claim 1, wherein
   the fastening tape has a proximal end attached to said one of the side flaps and a free end opposite to the proximal end,
   a width of the fastening tape in the longitudinal direction of the absorbent main body reduces from the proximal end towards the free end,
   a difference between the width of the fastening tape along the longitudinal direction of the absorbent main body at the proximal end, and the width of the fastening tape along the longitudinal direction of the absorbent main body at the end of a hook sheet existent region towards the proximal end, is 7.5 mm or less, and
   the hook sheet existent region is a region of the fastening tape existent region where the hook sheet is provided.

7. The disposable diaper according to claim 6, wherein the difference is 5.0 mm or less.

8. The disposable diaper according to claim 1, wherein an outer surface of the base sheet, which is opposite to an inner surface on which the hook sheet is provided, has substantially the same form or the same color tone as an outer surface of the absorbent main body.

9. The disposable diaper according to claim 1, wherein the basis weight of the nonwoven fabric is 30 to 120 g/m$^2$.

10. The disposable diaper according to claim 1, wherein the basis weight of the nonwoven fabric is 40 to 90 g/m$^2$.

* * * * *